US007033025B2

(12) United States Patent
Winterbotham

(10) Patent No.: US 7,033,025 B2
(45) Date of Patent: Apr. 25, 2006

(54) INTERACTIVE OCCLUSION SYSTEM

(75) Inventor: Chloe Tyler Winterbotham, Chicago, IL (US)

(73) Assignee: Virtocc, Inc., Chicago, IL (US)

( * ) Notice: Subject to any disclaimer, the term of this patent is extended or adjusted under 35 U.S.C. 154(b) by 371 days.

(21) Appl. No.: 10/150,310

(22) Filed: May 17, 2002

(65) Prior Publication Data

US 2003/0214630 A1 Nov. 20, 2003

(51) Int. Cl.
*A61B 3/00* (2006.01)

(52) U.S. Cl. .................................................... 351/203

(58) Field of Classification Search .................. 351/44, 351/45, 49, 201, 203, 211; 359/275, 722
See application file for complete search history.

(56) References Cited

U.S. PATENT DOCUMENTS

| | | | | |
|---|---|---|---|---|
| 4,726,672 | A | 2/1988 | O'Brien | |
| 4,896,959 | A | 1/1990 | O'Brien | |
| 4,967,268 | A | 10/1990 | Lipton et al. | |
| 5,026,151 | A | 6/1991 | Waltuck et al. | 351/246 |
| 5,206,671 | A | 4/1993 | Eydelman et al. | |
| 5,264,877 | A | 11/1993 | Hussey | 351/45 |
| 5,452,026 | A | 9/1995 | Marcy, III | |
| 5,737,060 | A | 4/1998 | Kasha, Jr. | 351/224 |
| 5,758,258 | A * | 5/1998 | Shoff et al. | 725/116 |
| 5,805,268 | A * | 9/1998 | Hosoi et al. | 351/211 |
| 5,821,989 | A | 10/1998 | Lazzaro et al. | |
| 5,861,936 | A | 1/1999 | Sorensen | 351/200 |
| 6,511,175 | B1 * | 1/2003 | Hay et al. | 351/45 |
| 2001/0050754 | A1 | 12/2001 | Hay et al. | |

FOREIGN PATENT DOCUMENTS

| | | | |
|---|---|---|---|
| DE | 3715850 | A1 | 11/1988 |
| EP | 0411821 | A1 | 2/1991 |
| WO | WO 98/02083 | | 1/1998 |
| WO | WO 00/72745 | A1 | 12/2000 |
| WO | WO 01/47463 | A1 | 7/2001 |

OTHER PUBLICATIONS

Bailey JL, Lovie JE, New Design Principles for Visual Acuity Letter Charts. Am J Optom Physical Optics 1976; 53:740-6.

Pelli OG, Robson JG, Wilkins, AJ. The Design of a New letter chart for measuring contrast sensitivity. Clinvision Sci 1988; 2:187-199.

Fielder AR, Irwin M., Auld R, Cocker KD, Jones HS, Mosely MJ; compliance in amblyopia therapy: objective monitoring of occlusion. Br J Ophthalmic of 1995; 79:585-589.

* cited by examiner

*Primary Examiner*—George Manuel
(74) *Attorney, Agent, or Firm*—Jenner & Block LLP

(57) ABSTRACT

An interactive occlusion system, including software and hardware, for the treatment of amblyopia using virtual reality or other physically interactive or perceptually immersive three-dimensional or two-dimensional computer generated simulations, in which the patient's occlusion compliance and usage time during occlusive and non-occlusive periods can be precisely recorded and the patient's visual acuity can be accurately measured to be provided to the clinician, as well as the capacity for entering prescriptions and treatment plans for individual patients and restricting individual access to that patient's prescription and treatment plan while allowing non-occlusive operation of the system after the prescribed occlusion time or for non-patient users.

28 Claims, 3 Drawing Sheets

2/3

INTERACTIVE OCCLUSION SYSTEM

FIELD OF THE INVENTION

The present invention pertains to an interactive occlusion system, including computer software and hardware, for the treatment of amblyopia using virtual reality or other physically interactive or perceptually immersive computer generated three dimensional or two dimensional environments including the precise measuring of treatment compliance and recording of visual acuity during such treatment, as well as the capacity for restricting individual access to each patient's prescribed treatment plan. More particularly, the present invention pertains to a system in which the clinician can program an individual treatment plan for each patient using a virtual reality system or other computer-generated physically interactive or perceptually immersive setting for performing visually demanding tasks while the system selectively occludes the patient's eye(s) as the clinician prescribes. During such treatment, the patient is presented with tasks requiring varying levels of visual acuity to progressively exercise the amblyopic eye, while protecting against creating amblyopia in a normal or less amblyopic eye. The system records the amount of time that each eye is occluded as well as the visual acuity level of the patient for clinician monitoring.

BACKGROUND OF THE INVENTION

Amblyopia, epidemiologically the most common vision impairment, is an ophthalmic condition usually beginning in early childhood and requiring immediate treatment in order for normal eye-brain visual pathways to develop. Most commonly unilateral, the cause of the problem in amblyopia is that, although there is no obvious structural abnormality in the eye, there is a problem with central fixation that can cause eccentric fixation in trying to see a target toward which the two eyes align or try to align. The anatomical centers of vision, the fovea and its most sensitive center the foveola (both contained in the macula) are so crucial to precise vision and visual stimulation that the further from the foveola that fixation occurs, the larger the compensatory or eccentric area must be. Although some eccentric areas can see surprisingly well, when vision is not central, a suppression scotoma, or area not seen by the eye, develops at or near the foveola, fovea or macula, getting worse as fixation moves further from the macula. Unless the scotoma is small enough for remaining central vision to compensate, which will not happen in the retinal periphery where Snellen equivalent visual acuity drops to 20/200 or worse outside the macula, the brain can start to suppress the image from the non-fixating eye, stopping the visual stimuli necessary to reach the visual pathways into the brain, arresting normal visual development and creating amblyopia. The drive for fusion necessary between the two eyes to see one image for stereo vision will not be sufficient. Amblyopia can be treated by interrupting binocular vision with occlusion of the sound eye, thereby stopping suppression of the amblyopic eye and allowing it to work. Significantly, without treatment, if the visual pathways in general do not develop, visual stimuli in later life will not compensate sufficiently for complete perception, nor will stereoscopic vision be possible. Although treatment does not guarantee stereoscopic vision, early and effective treatment increases the possibility of improving stereoscopic vision. Additionally, if amblyopia is left untreated and the sound eye becomes permanently damaged, for whatever reason, the amblyope will be forced to rely solely on the amblyopic eye. This reliance on the already visually impaired amblyopic eye can leave the amblyope with either blindness or serious vision loss.

For any binocular vision, the two eyes move in the same direction in order to see a target. With or without alignment of both eyes, each eye sees its own separate image(s) from the binocular retinal rivalry or disparity of the perceived images created by the distance between the two eyes, driving fusion to bring the images together in a way that the brain can interpret in a logical three dimensional or stereo perceptual image. With misalignment of the two eyes, such as with strabismus, and particularly in unilateral esotropia, a common cause of amblyopia, one eye does the work of central fixation. There are theories that amblyopia can develop in the crossing, non-fixating eye because either it experiences confusion during binocular vision trying to see images which overlap without accurate fusion between the two eyes, or the two eyes experience diplopia when unable to fuse. Over time, inability to fuse can cause the suppression of vision in the non-fixating eye which becomes amblyopic.

In completely cross-fixating bilateral strabismus, visual acuity might be equally good or bad between the eyes with no amblyopia, but there may be suppression, such that amblyopia could develop. The necessary developmental best corrected visual stimulation is obtainable during a long enough alternating period of central fixation, but bilateral strabismus patients must be monitored for the development of amblyopia. All strabismus patients must use best corrected vision, whether refractive error is spherical or astigmatic. Aligning or straightening the eyes with either prisms in the lenses or surgery is an important element of treatment in the course of strabismic management. Alignment, however, can cause secondary problems and will not conclusively correct amblyopia. Prisms also do not directly correct refractive error. Accommodative esotropes whose near vision can be corrected with a bifocal add to bring the converging fixating eyes' retinal images into better view in addition to their distance, usually hyperopic, correction, can do well but must be watched because amblyopia impairs the ability to control accommodation.

All amblyopes must have best corrected vision in both eyes for treatment to be effective. Other treatable problems, which must still be watched because of potential central suppression, include anisometropia, where the eye sizes can be markedly different, as in axial myopes who have longer eyes than hyperopes. The issue lies in best corrected vision, because, whether uncorrected or corrected the images produced are different sizes, a phenomenon known as aniseikonia, perceived best after correction of refractive error. Once corrected, the image is minified by lenses for treating myopia and magnified by lenses for treating hyperopia, so aniseikonia remains and is sharply and uncomfortably perceived, driving one eye to prefer fixation and creating amblyopia. Contact lenses can help, but careful instruction with parents and the patient is necessary continually and amblyopia can still develop. In some cases of smaller refractive differences known as isoametropia, eye sizes may make no difference, but binocular amblyopia can develop if refractive error is not corrected. If corrected early enough, normal fusion and stereopsis usually develop instead of amblyopia. Additionally, severe astigmatic refractive error can produce amblyopia along ametropic meridians, which may limit the effectiveness of astigmatic contact lenses in treating meridional amblyopes later in life.

Some of the most tragic and intractable forms of amblyopia are deprivational, such as a congenital cataract, even if removed at infancy and treated with contact lenses immediately and diligently. Corneal opacities, either congenital or early traumatic, sometimes can be treated surgically, but the best correction post-op such as with a contact lens does not often yield good vision. Corneal and any media opacity can lead to amblyopia. Ptosis, where the lid droops over the line of vision, can have better results with surgery. Retinal or optic nerve disorders, or any central brain disease or damage affecting the visual pathways, can lead to permanent uncorrectable vision loss or deprivation effects. Certain retinal and central brain diseases are not always detectable in early patient examinations, leading to treatment delay that can cause amblyopia. Another indication of amblyopia that can reduce visual acuity is nystagmus. In severe nystagmus, the eye cannot hold still long enough to focus though there may be improvement with amblyopia therapy. Regarding the various theories about amblyopiogenic mechanisms, other than deprivational causes or refractive errors, misalignment of the foveas appears to be a consistent cause of amblyopia. Amblyopic misalignment should be differentiated from monofixation and anomalous retinal correspondence. In all treatment plans, the clinician must ensure that the patient utilizes best corrected vision.

In most cases of amblyopia, there will never be development of full stereopsis, and fusion requires amblyopia treatment to make any progress. If treatment doesn't work, many amblyopes learn to rely on monocular cues to navigate the perspective of a three-dimensional world. One example of such a monocular cue is motion parallax, in which the patient observes the relationship between objects in the patient's field of view as the patient moves in relation to the objects. For example, when the patient moves and his or her perspective changes, objects that are closer to the patient appear to move more in relation to a distant background than objects that are further away.

Visual acuity describes several areas of visual thresholds, including spatial discrimination and minimum separable visual acuity. The ability of a patient to resolve spatial patterns is defined at the smallest visual angle at which the patient can discriminate two separate images or objects. Clinicians, however, prefer the concept of minimum separability, which is the angle that the smallest recognizable symbol subtends on the retina. Minimum separable acuity depends on two things, first, packing density of photoreceptors in the fovea. This is potentially related to amblyopia because of the possible phenomenon of the retinal spread of photoreceptors in some cases contributing to eccentric fixation and therefore causing amblyopia.

The second important consideration under the minimum separability category is object contrast. Contrast sensitivity is an important modern element for testing eye disease and treatment progress, as discussed in Pelli D G, Robson J G, Wilkins, A J., "The Design of a New Letter Chart for Measuring Contrast Sensitivity", Clin. Vision Sci. 1988; 2:187–199 [Pelli-Robson], the contents of which are herein incorporated by reference.

The most commonly used and referred-to chart for testing visual acuity at both distance and near is a Snellen equivalent scale. The Snellen scale identifies normal visual acuity as the ability of a patient to resolve spatial patterns, usually tested by alpha-numeric characters, where each character as a whole subtends a visual angle of five minutes of arc at a distance from the patient of 20 feet (or 6 meters) at distance or 12 inches (or 33 centimeters) at near. For metric conversion, a type of standardized test chart can be placed at four meters and can also be used at one to two meters distance for the low-vision patient. The four meter chart leaves the patient 0.25D (diopters) myopic, which can be compensated for with a refractive lens at testing to correct to infinity at distance. Images or other non-literate testing techniques, such as those used in preferential looking, pointing responses, Allen cards, cover testing, HOTV matching, and the illiterate "E" test, are some of the methods used for testing younger, illiterate and non-verbal patients. Amblyopia can be under- or over-estimated in this patient group, making the treatment plan crucial to the improvement of amblyopia.

Snellen chart alpha-numeric systems do not change size in a mathematically exact progression except at the lower levels. Progression of letters using Snellen is a linear function, which is not a mathematically effective measuring system. Bailey and Lovie developed a logarithmic conversion chart known as the logarithm of the Mininum Angle of Resolution ("logMAR"). On logMAR charts, letter sizes progress geometrically, not linearly, using decimals that can easily be converted to Snellen (e.g., 0.0 is equivalent to 20/20). See Bailey I L, Lovie J E, New Design Principles for Visual Acuity Letter Charts. Am J Optom Physical Optics 1976; 53:740–5 [Bailey-Lovie].

Especially in the United States, many clinicians measure visual acuity on the Snellen scale. Normal visual acuity is described as "20/20", where the numerator refers to the distance of the testing object from the patient in feet, and the denominator refers to the distance in feet at which the testing object subtends a visual angle of 5 minutes of arc. For example, if the patient is unable to resolve a spatial pattern at 20 feet (or its equivalent relative to the spatial pattern's size) that would subtend a visual angle of five minutes viewed at 60 feet (or its relative equivalent), the patient is said to have 20/60 visual acuity. One difficulty clinicians face in measuring visual acuity, especially in amblyopes, is the crowding phenomenon, also known as contour resolution or contour interaction, in which patients have difficulty resolving closely spaced contours and recognizing the patterns formed by the contours. For example, a patient may be able to recognize a single image in isolation at a smaller level of visual acuity than when the image is presented with other images. In amblyopes, the magnitude of the drop in measurable visual acuity in crowding situations can be larger than other patients. For purposes of visual acuity testing, even the interaction between a single symbol and the line formed by the edge of the chart can cause contour resolution problems and corresponding difficulties in accurately measuring visual acuity.

Traditionally, amblyopic patients have been treated by a process of occluding the patient's sound eye by covering the eye with the standard band-aid patch, the current usual standard of care. Such occlusion forces the amblyopic eye to work to resolve images, and therefore become stronger by developing the brain's visual pathways over time. Gradually, if compliance patching is successful, the visual acuity of the amblyopic eye can improve. Such treatment has been successful, but has significant drawbacks. The patches are uncomfortable, and until the vision in the amblyope's eye has recovered to normal visual acuity (if ever), the amblyope's reduced vision exposes the wearer to risks such as injury from not having peripheral vision on the patched eye to see approaching objects during normal activity. Because patch occlusion is normally used on young patients, wearing the patch can also expose the patient to teasing by other children. Other issues include skin irritations from the patch and the materials used to attach it. Because of these issues, patients frequently do not wear the patch for the full amount of time prescribed by the clinician, causing parental or guardian distress. This makes it difficult for a clinician to measure the amount of time that the patient's sound eye was actually occluded, known as the compliance time. The clinician must rely on the patient and the patient's parents to ensure that the patient wears the patch, and to estimate and report the actual compliance time. Patient and parent compliance estimates are notoriously unreliable, as either there is a general desire to please the clinician by reporting what the patient or parent thinks the clinician want to hear, or the patient and/or parent may give up estimating compliance time altogether. Because of these deficiencies, the clinician cannot determine the actual compliance time and is frustrated by the inability to accurately prescribe future treatment.

Other common methods of treatment include penalizing the patient's sound eye with a glasses lens with an incorrect prescription to defocus the sound eye. Using contact lenses is preferable once the techniques of wearing and cleaning has been mastered by the parents or an age-appropriate patient. For example, there are black lenses to completely occlude, which have the disadvantage of the patient knowing occlusion is occurring. Bilateral contact lenses, one to defocus and one to provide best corrected visual acuity can be used and switched on a schedule, but take vigilance to know which goes into which eye. It works most ideally in binocular amblyopes with similar refractive errors in each eye so that spares can be easily replaced. Another penalization method is the use of drugs such as atropine to cause the non-amblyopic eye to dilate and defocus. Lens penalization is undesirable because it is easy to circumvent by removing the glasses or contact lens. Drug penalization methods are not ideal because bioavailability, which varies from patient to patient, causes the drawback that the drug can affect other organs including the amblyopic eye, causing it to defocus, thereby increasing the risk of no improvement in the amblyopic eye, or worse, that the better eye becomes amblyopic. Variable bioavailability also reduces the amount of measurable clinical office data on the patient's improvement. The unpredictability of the correct dosage and application of the drug makes the correct prescription cumbersome for the clinician. Once again, the clinician must rely on the patient, or the patient's guardian for young children, to accurately apply the best-guess dosage.

Because there has been no way to accurately enforce or measure treatment compliance time with patch occlusion, lens or drug penalization, it has been very difficult for a clinician to judge the penalization in any form and prescribe accordingly. Current estimates of the necessary amount of compliance time for effective treatment vary widely, from minutes per day to hours. Similar issues exist with prescribing the correct duration and frequency of the occlusion therapy, which varies from patient to patient.

Fielder A R, Irwin M., Auld R, Cocker K D, Jones H S, Mosely M J, "Compliance In Amblyopia Therapy: Objective Monitoring Of Occlusion", Br J Ophthalmol 1995; 79:585–589, [Fielder] describes one device designed to improve monitoring of patch compliance. Fielder discloses an occlusion dose monitor ("ODM") that collected compliance data using a battery operated data-logger connected to the patient's patch. In Fielder, parents are still required to keep a parallel diary to monitor patch contact. Fielder notes that compliance is still difficult to measure and only discloses measuring compliance in the context of band-aid patching. Fielder does not disclose any interactive system for treating amblyopia, and Fielder's device shares the attendant disadvantages of band-aid patch occlusion as described above.

Interactive occlusive systems for the treatment of amblyopia are known in the art. See U.S. Pat. No. 4,726,672 to Diamond [Diamond I] and U.S. Pat. No. 4,896,959 to Diamond [Diamond II]. The amount of interactivity in such systems, however, is limited. Diamond I and II describe a system with LED displays limited to displaying characters that, through the use of mirrors and lenses, appear to be placed at a certain distance from the patient. The non-amblyopic eye is occluded using the device, and when the patient can recognize the displayed character, the patient must press a button to indicate which character was seen. As the treatment progresses, the patient is shown increasingly distant objects. Diamond I and II also require the patient to estimate the amount of time spent occluded and mail the occlusion time to the clinician. This complexity limits the use of the system to older patients, bypassing younger patients in which occlusion treatment is most effective. Also, using older, lower-risk patients requires fewer safeguards than younger patients, and despite showing some improvement in subjects with severe amblyopia, Diamond does not provide a representative sample of the population known to be in need of standard of care. The limited interactivity of the system also reduces the effectiveness of the therapy. The more the patient is mentally focused during the treatment, the harder the amblyopic eye will work, with potential improvement. The limited amount of characters displayed by the device also increase the risk that the patient will memorize the sequence of characters, or guess the correct character without actual recognition. Such limitations limit the ability of the clinician to rely on the results of the system. A further disadvantage of the Diamond systems is that the patient is aware when he or she has reached a certain target visual acuity level, because the patient is required to report the information to the clinician.

U.S. Pat. No. 5,206,671 to Eydelman, et al [Eydelman] describes an amblyopia treatment system using a personal computer for displaying various images to the amblyope, including pictures and cartoon images while the non-amblyopic eye is occluded. Eydelman also discloses the concept of using a video game to engage the patient's attention. Eydelman does not disclose, however, any form of occlusion other than the standard patch. While Eydelman discloses recording results, and monitoring and adjusting visual parameters, Eydelman does not disclose a method for precisely measuring occlusion compliance time. A further detriment to such systems is that with patch occlusion, the patient is conscious of which eye is occluded, which may limit the effectiveness of the treatment. Both the Diamond systems and the Eydelman system also require an auditory cue to the patient in order to indicate targeting success or failure, restricting use of the system by patients with hearing problems.

Previous interactive systems also suffer from a lack of safeguards on improper use. In order to meet or exceed the current standard of care, treatment systems must be very careful to avoid creating amblyopia in non-amblyopic eyes. This can occur either where the patient exceeds the recommended occlusion time for the non-amblyopic eye, or if the patient allows a non-amblyopic friend to use the treatment system. This concern is especially prevalent in younger patients.

Additionally, previously known interactive treatment systems utilize a standard downward progression of image size. Once the patient recognizes a character or an image at a certain visual acuity level, the next image or character is displayed at the next highest acuity level. This allows the patient to more easily memorize the progression of treatment, and may lead to a patient correctly guessing the correct image without actually achieving the indicated level of visual acuity.

Shutter-glasses are also known in the art for performing occlusion for treatment of eye disorders. U.S. Pat. No. 5,452,026 to Marcy [Marcy] describes a system for performing occlusion using LCD shutter glasses by connecting the LCD shutter glass for each eye to an independent timer system for occluding each eye according to independent duty cycles. Marcy, however, only discloses the use of the shutter glasses for occlusion as a treatment for improving stereopsis, not amblyopia, and furthermore does not suggest any mechanism for utilizing the shutter glasses in an interactive system for accurately measuring the compliance time and visual acuity.

The use of shutter glasses for simulating stereo vision in a computer application is also well known in the art. See U.S. Pat. No. 4,967,268 to Lipton [Lipton], the figures and specification of which are herein incorporated by reference. Lipton describes a system in which the user wears LCD shutter glasses where the shutter for each eye alternates between transparency and opacity according to a predetermined frequency above the human flicker fusion rate. The frequency at which the shutters are switched is synchronized with the display of visual frames by the computer, such that when the left shutter is opaque, the user is presented with the appropriate image for the user's right eye, and vice versa for the right shutter and left eye. In such a manner, the user's brain fuses the two images together to form one stereo image. Lipton does not disclose or suggest any application of the invention to treating amblyopia, or for measuring compliance time or visual acuity during treatment of amblyopia.

Furthermore, previous systems do not address the problem of crowding. In the real world, objects are not isolated as single images, and therefore systems that only treat amblyopia using single images do not accurately measure the patient's progress.

Because of the limitations of existing amblyopia treatments, there exists a continuing need for a fully interactive, individualized virtual reality occlusion system for treating amblyopia and precisely monitoring and recording compliance and visual acuity during such treatment.

SUMMARY OF THE INVENTION

The present invention overcomes the limitations of the prior art by providing a system for treating amblyopia with an individualized, interactive occlusive system using computer hardware and software wherein the patient is immersed in a task-intensive physical activity in a virtual reality or other physically interactive or perceptually immersive three-dimensional or two-dimensional computer-generated setting, in which the patient's occlusion compliance and usage time during occlusive and non-occlusive periods can be precisely recorded and the patient's visual acuity can be accurately measured to be provided to the clinician.

Prior to starting treatment, the clinician will review the patient's case and prescribe an appropriate treatment regimen individualized for that particular patient. This treatment regimen will include the duration of treatment, how frequent treatment sessions should be, the number of treatment sessions, and how much occlusion is required per session for each eye. Other treatment regimen parameters may include the patient's baseline visual acuity and the amount of testing for crowding and contrast sensitivity. For the purpose of the present invention, visual acuity can be measured using either the Snellen, logMAR or any other visual acuity measurement scale.

During treatment, the patient accesses a computer system that runs the treatment application. The term computer includes any microprocessor-based device capable of running software applications. The treatment system is individualized, such that the system is able to treat multiple patients, but each patient is only able to run the treatment program that has been prescribed by the clinician for that specific patient, either by password-protecting the treatment system, voice or other biometric recognition or other protection method. This prevents improper access to the system and avoids creating amblyopia in non-amblyopic eyes of any user, whether the user is a patient or non-patient. If the treatment system is accessed by someone other than a patient, or used past the prescribed treatment time by the patient, the treatment system will operate without occluding either of the user's eyes in order to prevent causing amblyopia.

The treatment system runs a virtual reality application, or some other computer-generated physically interactive or perceptually immersive three-dimensional or two-dimensional graphics application that gives the patient a sense of being physically or perceptually immersed in an activity. Preferably, the graphical simulation is displayed large enough to engage the patient's peripheral vision in order to give the patient the sensation of being inside a virtual world, through some combination of the size of the monitor and the proximity of the display to the patient. Ideally, the patient is using a fully-immersive virtual reality system displaying images for the patient's entire field of vision, such as the CAVE Automatic Virtual Environment ("CAVE") virtual reality system. The present invention also works, however, with wide-screen displays capable of engaging the patient's peripheral vision, such as the CAVE ImmersaDesk system and goggles containing LCD screens, as well as standard desktop monitors, projectors used to display graphical images from computers, interactive televisions and other display media. Furthermore, the ideal graphics application for the present invention is a fully-immersive virtual reality application. The present invention works, however, with any three-dimensional or two-dimensional computer-generated simulation. In any case, the patient perceives movement in a way that is physically or perceptually immersive. The treatment application can also be any application that interests the patient, such as a game, exercise, puzzle, test or other interesting activity.

The patient wears a device that can selectively occlude vision of either of the patient's eyes, such as LCD shutter glasses or some other type of goggle or headset device. The treatment should be used with the patient's best-corrected vision, so the glasses or goggles will be able to be used over prescriptive lenses, including correctly positioned bifocals for accommodative esotropes. The duration of occlusion is controlled and measurable by the computer system. For example, if the patient's right eye is amblyopic, the computer could occlude the left eye for a precise length of time specified by the clinician. In order to more fully exercise the amblyopic eye and keep the interactivity level of the treatment system high, which improves compliance, the patient should not be aware which eye is being occluded at any given time. Based on the clinician's instructions, the computer could also operate such that the amblyopic eye should be occluded for a clinician-programmable period of time in order to exercise the non-amblyopic eye, preventing the treatment from inadvertently causing amblyopia in the sound eye, or operate such that neither eye is occluded after the prescribed treatment time. It is also important for the system to record and report to the clinician the amount of time during which the system was used in a non-occluding manner in order to judge the effectiveness, interactivity and patient appeal of the treatment system. For example, if the patient is enjoying a treatment application such as a game, the patient can continue playing the game after the prescribed treatment. This allows the patient to see the treatment as an entertaining experience rather than as an assignment. It should be noted, however, that the treatment system could also be used by the patient for performing homework assignments.

During the treatment, the patient engages in a set of activities that are designed to exercise the amblyopic eye while simultaneously measuring the patient's compliance time and visual acuity level. For example, the patient could be presented with an object selected from a set of objects and displayed at a programmable distance. When the amblyope can correctly identify the object, either by selecting an appropriate image with a pointing device or other selection mechanism, the computer can record how far away the object was when the patient identified it, as well as the visual acuity level of the object. Because the patient is immersed in asimulated environment, the computer system can present the image to appear as if it were a certain distance from the patient and scaled to the appropriate size for the patient's visual acuity level. Where the patient is fitted with a position tracking device such as a magnetic position sensor, the computer can determine the patient's distance from the display and scale the images to take angular magnification into account. In cases where a position tracking device is not feasible, the patient's view could be fixed at an appropriate position and distance using a headrest, and the displayed images calculated accordingly. As the patient's visual acuity improves, the size of the objects can be scaled to smaller visual acuity levels to further exercise the amblyopic eye, but unlike the prior art, the object size can be increased or decreased in random order in order to avoid memorization concerns. The computer can also present the object as moving any direction in the simulated environment, either toward, away from, lateral, or vertical to the patient.

The clinician can review the recorded results of these activities, and either change the prescription or maintain a standard progression of treatment. Also, the application can have certain measures programmed into it to ensure that the amblyope has actually progressed to a certain visual acuity level or has merely successfully guessed an object's identification through guessing or memorization. The set of objects from which the object to be identified is selected should contain enough objects to reduce the chance of successfully guessing, and the sequence in which objects are presented should be random or varied sufficiently to prevent memorization. The application can require the patient to correctly identify a certain number of objects at a visual acuity level to ensure that the patient has truly recovered visual acuity to that level before progressing to the next level. The application also is not limited to a strict downward progression of image size. The application can reduce or enlarge the object sizes as appropriate to further challenge the patient, or increase the number of images on the screen to determine whether the patient's visual acuity has also improved in crowding situations as well. The application can also simulate the patient moving around the simulated environment either towards or away from the object. This increases the actual or perceived physicality of the treatment, which not only increases the patient's interest in the treatment, and therefore the treatment's effectiveness, but also improves the amblyope's ability to navigate in realistic settings.

The system can record when the patient is being occluded, and can record if the patient has ended a treatment session before the recommended compliance time has been completed. Because the amount of occlusion time is cumulative over the patient's sessions, the system can automatically prescribe the appropriate occlusion time during the next session to compensate for the change in compliance time in the previous session. Additionally, the computer can register when the patient has reached the prescribed occlusion time and can operate the system in a non-occlusive manner without the patient's knowledge to avoid increasing the risk of creating amblyopia in the sound eye. Between treatment sessions, the clinician can review the patient's results and adjust the patient's prescribed treatment. The clinician can also monitor the patient's treatment session and make any changes necessary while the session is proceeding.

The present invention can be used in any location, either at the clinician's office, the patient's home, or other setting such as a school or after-school site. In such cases where the present invention is not located at the clinician's office, the clinician can provide the prescription in a portable digital format to the patient to control the treatment system during a treatment session. Operating the treatment system at locations other than the clinician's office allows the patient more flexibility for when the system will be operated, increasing compliance. For example, if the treatment system were located at a school facility, the patient could run the appropriate treatment application, which could be a peer computer assignment or an independent program prescribed by the clinician for use during the school day. A teacher or school nurse could receive the prescription file from the clinician and supervise the patient's use of the system. As described above, after the patient has completed the prescribed occlusion time, the patient could continue to run the treatment system in non-occlusive mode for either continuing to play the treatment application or performing school assignments on the computer system, with images or characters appropriately sized to the patient's visual acuity level. Additionally, if the patient has been instructed to perform classroom assignments on a computer, the patient could operate the treatment program to perform the assignment, making the patient's treatment plan more conforming to peer activities and easier for the teacher to manage. In locations where clinicians or other supervisory adults are present, the patient can also request help at any time and never feel isolated.

It is an object of the present invention to provide a clinician-directed system using virtual reality or other physically interactive or perceptually immersive three-dimensional or two-dimensional computer generated setting, either in a clinical setting, at a patient's home, school, or other patient-accessible site, for occluding the patient's amblyopic or non-amblyopic eye, or occluding neither, as appropriate, and immersing the patient in a simulated environment or other perceptually immersive interactive three-dimensional or two-dimensional computer-generated setting while causing the patient to perform visually demanding, task-intensive activities for exercising the patient's appropriate eye. During the treatment, the system can precisely record the patient's occlusion time and accurately measure the patient's visual acuity level. The clinician can then review the results and make any necessary adjustments to the treatment plan.

It is a further object of the invention to provide a system with an individualized treatment regimen, wherein a patient can only access that patient's treatment, and such that if the system is operated without an access code, neither eye is occluded so that the system avoids creating amblyopia either in the patient or in anyone else using the system.

It is a further object of the invention to provide a system where the clinician can enter a prescription for a specified amount of occlusion time for each eye. As treatment progresses, the clinician will review the results of the treatment and can modify the prescription based on the patient's individual progress. The system can record for the clinician the patient's total usage of the system, including both occluding and non-occluding usage in order for the clinician to judge the effectiveness of the treatment.

It is a further object of the invention to provide a system wherein the visually demanding tasks performed by the patient include identifying objects at a programmable visual acuity level, as indicated by the objects' size and distance. The objects may be stationary or moving in the simulated environment, and the system measures the patient's visual acuity level based on the distance at which the patient was able to identify the objects. The system may also present the patient with objects of varying sizes to ensure that the patient has actually progressed to a certain level of visual acuity.

It is a further object of the invention to provide a system where the treatment can be provided either in the clinician's office or other clinical setting, the patient's home, or potentially anywhere, such as a school or after-school site, as improvements in technology shrink the hardware size necessary to run the system.

It is a further object of the invention to provide a system which presents the visually demanding task of chasing objects through a three-dimensional setting, where the patient and the objects are able to move independently through the simulated environment.

DETAILED DESCRIPTION OF THE INVENTION

The present invention utilizes virtual reality, or other physically interactive or perceptually immersive computer-generated three-dimensional or two-dimensional settings, to treat amblyopia using computer-controlled occlusion of a patient's eyes while precisely recording the patient's occlusive and non-occlusive usage of the system and accurately measuring the patient's visual acuity in a task-intensive treatment application.

Figure 1:
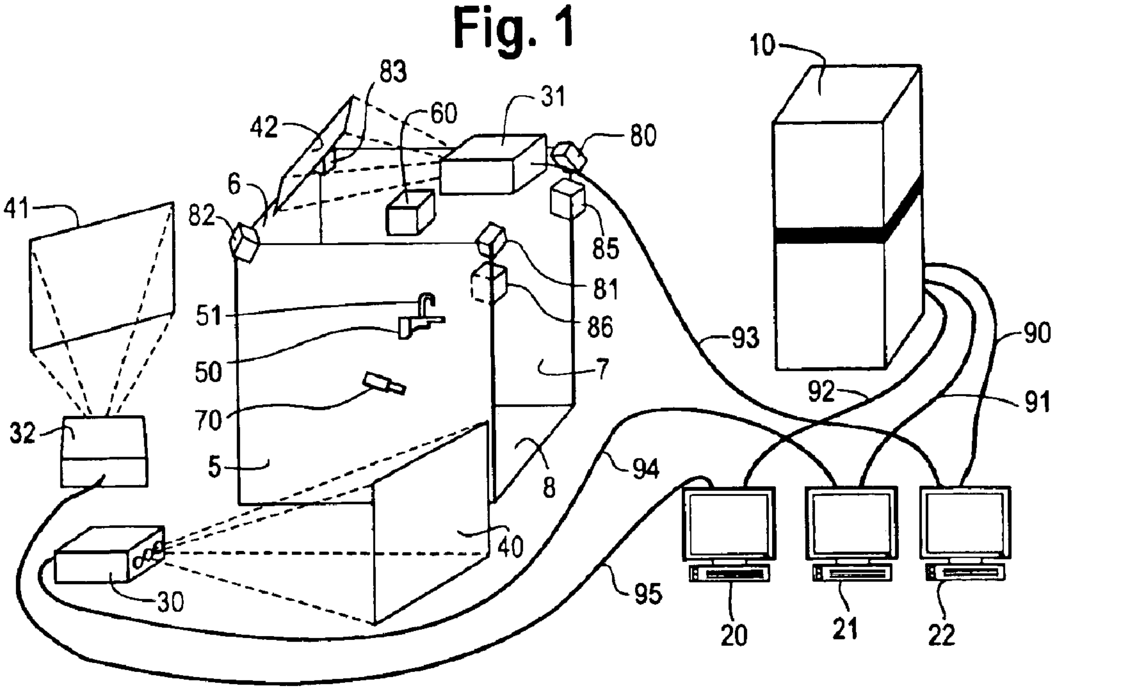
FIG. 1 is a perspective drawing of a virtual reality treatment system.

FIG. 1 shows a perspective drawing of a preferred embodiment of the virtual reality hardware for the treatment system, utilizing the CAVE virtual reality system. The patient stands inside a room with walls 5, 6, 7 and floor 8. The walls 5, 6, 7 of the CAVE are translucent, such that images may be projected on the outside surface of the walls 5, 6, 7 and still be visible on the inside surface. The preferred embodiment utilizes a central computer system 10 capable of displaying realistic three-dimensional graphics, such as a Silicon Graphics Onyx computer, and utilizing virtual reality software capable of rendering virtual reality scenes, such as the CAVElib software package. The central computer system is connected to projectors 30, 31 32 that receive the graphics signal to be displayed through connecting cables 90, 91, 92, 93, 94, 95. The preferred embodiment may also contain video monitors 20, 21, 22 connected between the central computer 10 and the projectors 30, 31, 32 in order for external observers, such as a clinician, to view the images that the patient is currently viewing and monitor the patient's activities. Because the projectors 30, 31, 32 must be a certain distance from the CAVE walls 5, 6, 7 to create a correctly sized image, the images are first projected onto mirrors 40, 41, 42 that in turn reflect the projected images onto the walls 5, 6, 7 to minimize the overall size of the CAVE. The projectors 30, 31, 32 and mirrors 40, 41, 42 are located outside the CAVE walls 5, 6, 7 and project onto the outside surface of the translucent walls 5, 6, 7. The patient, not shown in FIG. 1, sees the resulting projected image from the CAVE on the inside surface of the walls 5, 6, 7. Alternatively,'the walls 5, 6, 7 of the CAVE could be opaque and the projectors 30, 31, 32 could be positioned inside the CAVE and project the images directly onto the inside surface of the CAVE walls 5, 6, 7. Not shown are additional projectors and mirrors for displaying images on all of the CAVE's walls 5, 6, 7 and floor 8 in order to provide the patient with the sensation of being fully immersed in the virtual world. Note that all of the components of the embodiment are capable of being connected either physically by cables, or by wireless communication.

The patient stands in the middle of the CAVE walls 5, 6, 7 while wearing a pair of LCD shutter glasses 50 capable of fitting over a patient's prescription lenses. The shutter glasses also contain a magnetic position sensor 51, which is tracked by the position tracking device 60. When the patient is wearing the glasses 50, the magnetic position sensor 51 and the position tracking device 60 provides the computer with not only the precise coordinates of the location of the patient's eyes within the CAVE, but also the exact direction in which the patient is looking. The computer 10 uses this information to determine what images to show the patient and, through the CAVElib software, adjust the perspective to match what the user would see when viewing real objects from that angle. Because the magnetic position sensor 51 and position tracking device 60 allow the computer system to track the patient's head position and orientation, which allows the graphics software to render the images with a viewer-centered perspective, motion parallax allows amblyopes to attain a level of depth perception.

Figure 2:
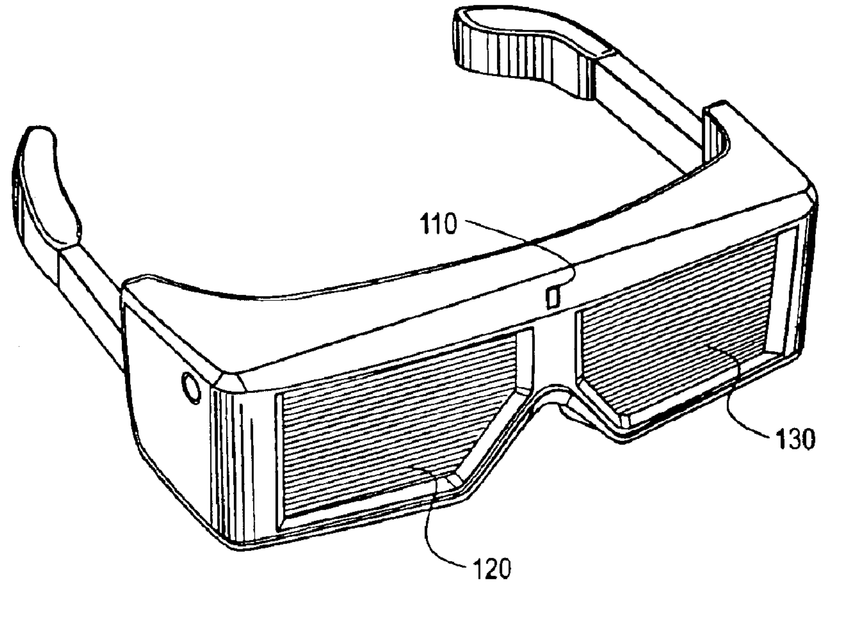
FIG. 2 is a perspective view of shutter glasses for performing occlusion.

Based on the patient's position, direction of view, and the application running during the patient's session, the computer 10 displays the virtual scenery specified by the treatment application software running on the central computer 10. The computer system 10 quickly alternates displaying frames from the perspective of the patient's left eye and right eye. The system has infrared transmitters 80, 81, 82, 83 mounted above the walls 5, 6, 7 and connected to the central computer system 10 and are capable of transmitting infrared signals to the shutter glasses 50. FIG. 2 shows a perspective view of a type of LCD shutter glasses capable of being used in the preferred embodiment. The shutter glasses contain an infrared receiver 110 keyed to receive infrared signals from the transmitters 80, 81, 82, 83. When the glasses receive the appropriate signal, the electronics in the glasses apply voltage to the LCDs in the lens covering the left eye 130, causing the left LCD lens 130 to be made opaque. When the glasses stop receiving that signal, the electronics stop applying voltage to the LCDs and the left lens 130 reverts to transparency. When the glasses receive the appropriate signal for the right eye, the electronics in the glasses apply voltage to the LCDs in the lens covering the right eye 120, causing the right LCD lens 120 to be made opaque. When the glasses stop receiving that signal, the electronics stop applying voltage to the LCDs and the right lens 120 reverts to transparency.

Referring again to FIG. 1, during normal operation of a CAVE system without the occlusion treatment system, the central computer system 10 alternates projecting images for the left eye and right eye at a certain frequency. The infrared transmitters 80, 81, 82, 83 are synchronized with the images being projected such that when the computer is displaying images from the perspective of the patient's left eye, the transmitter is sending signals to the shutter glasses 50 to cause the patient's right lens FIG. 2, 120 to become opaque. When the computer 10 is displaying images from the perspective of the patient's right eye, the infrared transmitters are sending signals to the shutter glasses 50 to make the left lens 130 opaque. In normal operation outside of the treatment application, this causes the brains of non-amblyopic users of the virtual reality system to fuse the two images together into a single stereo image, making the objects appear to be three dimensional and inside the plane of the walls 5, 6, 7 and floor 8. In amblyopes, the non-occluded image will not be true stereo, but will create the illusion of three-dimensionality. The shutter glasses 50 could also receive signals from the central computer system 10 using cables or wireless communication.

Occlusion for treating amblyopia can be achieved in the treatment system in multiple ways. For example, the glasses can be sent a steady signal to turn one of the lenses continuously opaque, controlled by the central computer for a specified amount of time. Additionally, the computer can perform occlusion by operating the shutter glasses in normal mode, alternating the opacity of the left and right lens, but projecting a completely dark image on all of the walls and floor when the lens covering the sound eye is transparent, and only displaying the virtual world to the user in the frames seen by the amblyopic eye.

The patient interacts with the virtual reality system using a pointing device such as a "wand" 70, a six degree of freedom device that allows the patient to interact with the virtual world in three dimensions, in contrast to the normal two degrees of freedom afforded by a standard desktop mouse selection device. The wand 70, like the shutter glasses 50 also contains a magnetic position sensor that allows the position tracking device 60 to track the exact position and orientation of the wand. Based on this, the central computer system can detect whether the coordinates of the wand's position in the CAVE correspond to the coordinates of an object in the virtual world, allowing the patient to select an object by striking it with the wand. The patient can also use the wand 70 to navigate around the virtual world. When the patient moves the wand 70 in space, the position tracking device 60 senses the movement and reports it to the central computer 10. For example, if the patient wants to move forward in the virtual world, the patient can hold the wand 70 with the top of the wand leaning forward. The position tracking device 60 detects the change in position of the wand 70, and as long as the patient holds the wand 70 in a forward position, the computer 10 will change the view displayed to the patient as if the patient were moving in space. When the patient wants to stop moving, the patient can hold the wand 70 perpendicular to the floor.

Additionally, the wand 70 can have buttons for the patient to press, and based on the position and orientation of the wand, the computer can compute whether a virtual ray projected from the wand's position 70 intersects any object in the virtual world. This allows the patient to select an object at any point in space by pointing the wand at the object and "shooting" the object. Other selection devices as known in the art could also be used, such as a mouse, keyboard, virtual reality gloves, a hand-held tablet such as a Palm Pilot, voice recognition or other selection mechanism. The system can also have audio speakers 85, 86 for presenting audio sounds either for success or failure indicators or ambient sound during the treatment session.

Figure 3:
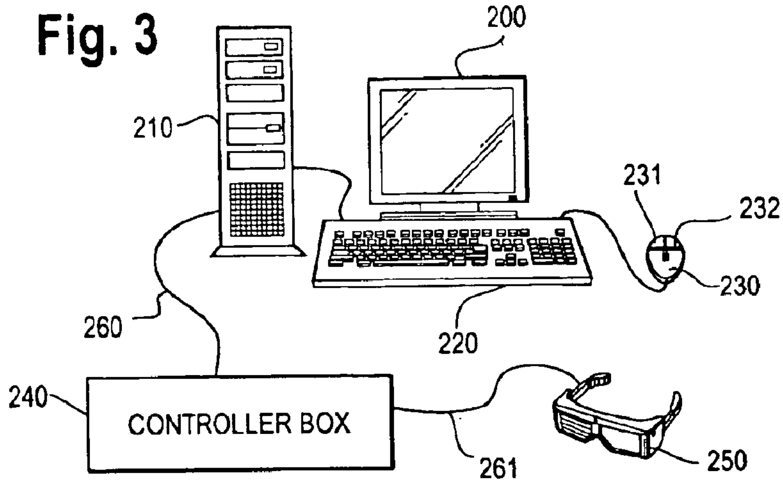
FIG. 3 is a schematic diagram of a second embodiment.

FIG. 3 shows an alternate embodiment of the hardware for the treatment system, utilizing a monitor 200 for the displayed images rather than the full CAVE system of FIG. 1. This embodiment also utilizes a central computer system 210 capable of displaying three-dimensional or two-dimensional graphics and containing graphics software, either virtual reality software or other software for displaying three-dimensional or two-dimensional graphics. The computer displays the images on a monitor 200. Preferably, the monitor 210 is large enough to encompass the patient's peripheral vision, such that the patient feels immersed in the virtual world or other simulated environment. The present invention works, however, on a standard desktop computer and monitor. The patient wears a pair of LCD shutter glasses 250 similar to those described above. Instead of receiving signals from infrared transmitters as shown in FIG. 1, 80, 81, 82, 83, the shutter glasses 250 are connected to a controller box 240 that is connected to the central computer 210. The treatment application works in a similar fashion as described above, displaying alternate images for the left and right eye. The controller box 240 receives signals from the central computer 210 synchronized with the frequency of the image display. Based on these signals, the controller box 240 sends signals to the shutter glasses 250 regarding which lens to make opaque and which lens should be transparent. The patient navigates through the simulated environment using a mouse 230 or other pointing device, and may use the buttons 231, 232 on the mouse 230 and the keys of the keyboard 220 similar to the buttons on the wand described above in the previous embodiment. In the case of very young children, or infants, a system such as FIG. 3 could be operated by the parent or guardian with the child sitting on the parent's lap and the child using age-appropriate pointing or grabbing mechanisms. The system can also operate such that multiple users can participate in the treatment program, so that parents, guardian or the clinician could participate with the patient to help guide the patient through the treatment program. In cases where each user has independent displays, such as goggles with LCD lens, each user could see the simulated environment from his or her correct perspective. In the case of the CAVE where only one image is displayed on the wall, the clinician, parent or guardian could view what the patient is viewing via the monitors as shown in FIG. 1, 20, 21, 22. Additionally, the parent, clinician or guardian could wear shutter glasses programmed to respond to a different signal than the patient's shutter glasses and the computer system could display the frames showing the virtual world from the helper's perspective alternating with the frames showing the patient's perspective. By synchronizing the signals to the patient's and the helper's shutter glasses with the frames being presented, the computer could present both users with the correct viewer-centered perspective.

The treatment system of the present invention can also be implemented using other virtual reality systems known in the art. For example, the patient could wear a pair of goggles where the goggles contain two separate LCD screens for displaying independent images to each of the patient's eyes. The image from the perspective of the patient's left eye would be displayed on the LCD screen in front of the patient's left eye, and the image from the perspective of the patient's right eye would be simultaneously displayed on the LCD screen in front of the patient's right eye. In such a system, the patient perceives a large display in front of the user. Occlusion can be easily performed in such a system by sending no image, or a completely dark image, to the eye being occluded at the given time. Additionally, as computer hardware shrinks in size, the treatment computer of the present invention could be worn by the patient, or could be contained in the glasses unit itself, eliminating the need for projectors or cables. In such an embodiment, however, the system would still require authentication to access a patient's prescription and operate in occlusive mode.

Figure 4:
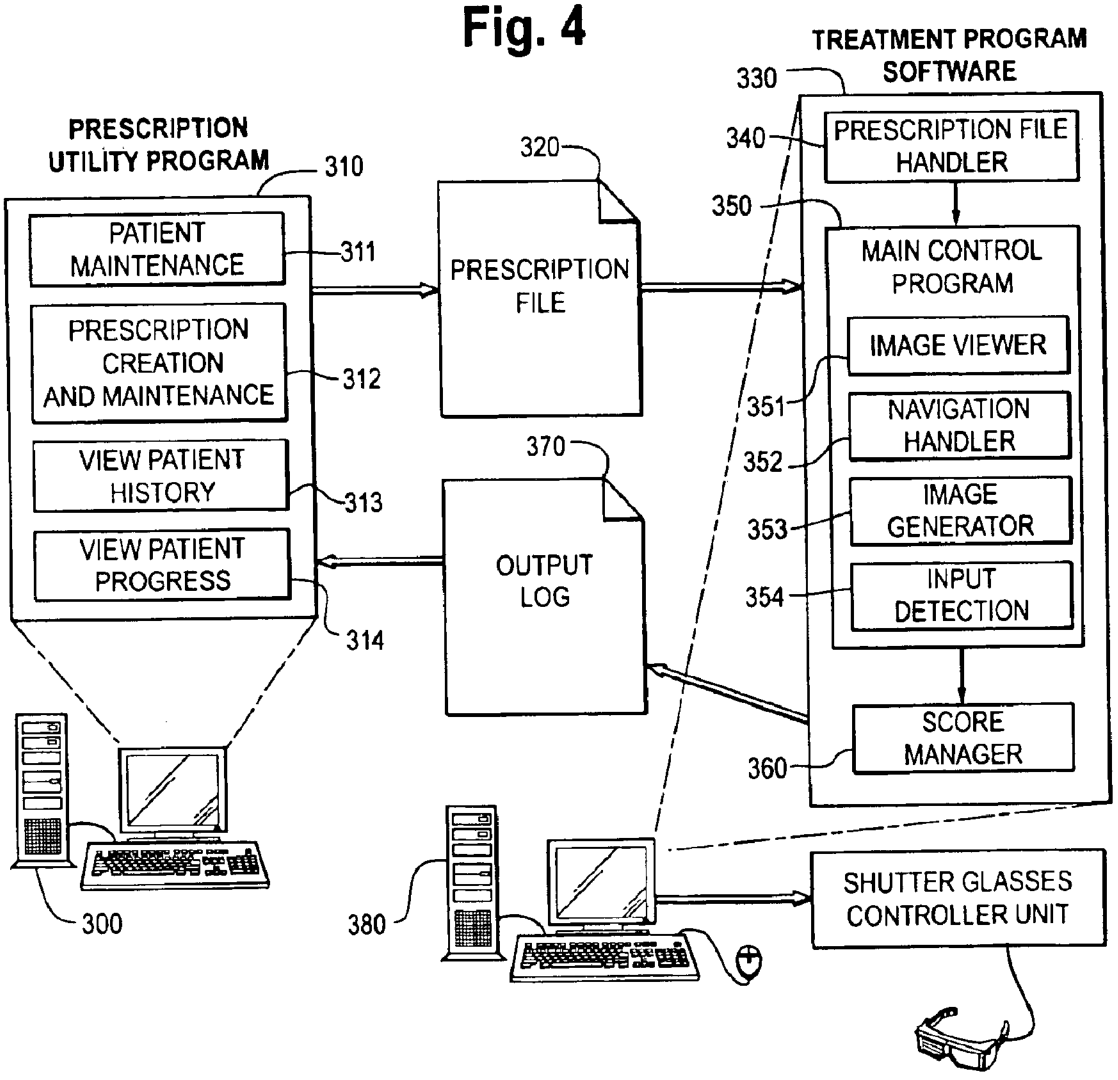
FIG. 4 is a schematic block diagram of treatment system embodiment, including hardware and software application components.

FIG. 4 shows a schematic block diagram of the software components of an embodiment of the treatment system. The treatment system contains two major components, the prescription utility program 310 and the treatment program software 330. Although FIG. 4 shows an embodiment of the treatment system in which the two components reside on separate computers 300, 380, the present invention can use any number of computer systems. The prescription utility program 310 and the treatment program 330 may even reside on the same central computer system such as FIG. 1, 10. Where separate computers are used, the treatment computer 380 and the clinician's computer 300 may be located in different physical locations, and may or may not be networked together. The treatment computer 380 may even be located at the patient's home. If the computers are networked, information can be easily transferred between the computers over the network and the clinician can monitor the patient's progress during the treatment session. If the computers are not networked, information may be transferred between the prescription utility program 310 and the treatment program 330 using a portable storage mechanism such as a floppy disk, compact disc, or flash memory stick, or the information may be communicated verbally or in writing for the clinician or patient, parent or guardian to enter manually. Additionally, the required files could be communicated between the treatment computer 380 and the clinician's computer 300 via e-mail or other electronic communications such as telephone dial-up connection.

The prescription utility program 310 allows the clinician to manage patient information, including the list of patients authorized to use the treatment system as well as the current and past treatment prescriptions and results information for each patient. The treatment program 330 is the application that performs the bulk of activities during an actual treatment session, including portraying the virtual world to the patient, controlling and recording the patient's occlusive and non-occlusive time, presenting the patient with task-intensive activities and measuring the results of the patient's treatment session, including the patient's indicated visual acuity level. For security reasons, the patients should not have access to the prescription utility program 310, either by maintaining the program on a separate computer 300 accessible only to the clinician, or by restricting access to the prescription utility program 310 application on a shared machine.

A clinician starts the treatment process by using the patient maintenance tool 311 of the prescription utility program 310 to create or edit a patient entry into a database, such as Microsoft Access or SQLServer. The patient maintenance database contains information about the patient such as the patient's name, password, a unique identification number in the system, and a list of the patient's prescribed treatments to date. The clinician can create a new treatment prescription 320 for the patient using the prescription creation and maintenance tool 312. The prescription 320 may contain information about the patient's prescription, such as a unique prescription identification number, the unique identification number of the patient the prescription is for, the number of treatment sessions, the length of treatment time for each session, the prescribed occlusion time for each eye, and the occlusion rate. The occlusion rate is the ratio of time the occluded eye should be occluded to the time that both eyes should be allowed to be open. Once a patient is entered in the patient maintenance database, the clinician can use the prescription creation and maintenance tool 312 to change the prescription 320 at any time during the treatment process. The prescription utility program can also maintain a history of all of a patient's prescriptions over the course of treatment.

Once the patient has been created in the system and the clinician has created a prescription for the system, the patient can begin running the treatment program 330 on the treatment computer 380. In order to ensure that each patient can only access that patient's own treatment, the treatment program 330 will use some form of user authentication, such as requiring the patient to enter the patient's correct password. It should be noted that other forms of user authentication are envisioned, such as voice recognition, fingerprint, or other biometric recognition. For systems geared to younger patients, including infants, the patient can be required to identify a particular image, such as a face, from a set of images. If the user of the system is unable to be authenticated as a patient with an active prescription, the system may either refuse to operate, or will operate solely in a non-occlusive mode in order to prevent the risk of creating amblyopia.

When the patient is authenticated, the patient's prescription 320 must be loaded into the treatment program 330. In the case where the treatment program 330 and the prescription utility program 310 reside on different computers, the prescription can be passed between the two systems as a prescription file 320. The file may be stored in a binary data format such that the patient is unable to view or modify the prescription, or the file may be encrypted to ensure patient privacy. In cases where the treatment program 330 and the prescription utility program 310 reside on the same computer, the treatment program 330 can read the prescription 320 directly from the prescription database. In either case the prescription file handler subsystem 340 of the treatment program reads the prescription information for use by the treatment program 330.

The main control subsystem 350 of the treatment program 330 is the part of the treatment application that controls the interaction with the user, and is responsible for sending the correct control signals to perform the specified amount of occlusion for the appropriate eyes at the appropriate times, as dictated by the prescription 320. The clinician will have prescribed the required amount of time for the normal eye to be occluded, but in order to decrease the risk of creating amblyopia in the sound eye, the clinician will also indicate the amount of time that the amblyopic eye should be occluded and the sound eye should be exercised. The amblyopic eye may also be periodically occluded in order to give the amblyopic eye rest, and in order to exercise the sound eye and prevent amblyopia from developing in the sound eye. The clinician may also indicate a proportion of occlusion of the sound eye to occlusion of the amblyopic eye, and the system will calculate the occlusion times based on the treatment session length.

The main control subsystem 350 of the preferred embodiment contains four software subsystems, although those skilled in the art will recognize that the number of subsystems may vary from embodiment to embodiment. The image viewer 351 is responsible for displaying the simulated environment to the patient, based on the patient's position in the simulated environment and the direction in which the patient is looking. The navigation handler 352 tracks the patient's position within the simulated environment and moves the patient within the world based on the patient's movement indications using the navigation mechanism such as the mouse, wand or keyboard. Once the navigation handler 352 has moved the patient to a new location in the simulated environment, the image viewer 351 redisplays the graphics representing the simulated environment from the user's new perspective. The navigation handler 352 can also be programmed to automatically navigate the patient to a new viewpoint, such as a treatment program designed for very young or disabled patients. Additionally, if the patient has identified a certain number of objects correctly, or if the patient has spent a specified amount of time in one area, the system could automatically navigate the patient to a new viewpoint at a new setting in order to further engage the patient's interest.

The image generator 353 is responsible for selecting the proper object for the patient for the patient's current task. The image generator 353 can select the object based on many different criteria, based on the treatment application being run. For example, where the patient's task is to identify an object, the image generator 353 can randomly select an object from the set of available objects at the correct size for the patient's task. The image viewer 351 is responsible for displaying the object to the user at the indicated size, distance and position from the user, and responsible for displaying the object as it moves through space. Potential treatment applications include any activity or exercise that presents the patient with an interesting and physically or perceptually immersive graphical task. The treatment applications are not limited to simple object recognition tasks, but could also include more sophisticated applications such as driving games that allow the patient to navigate through the simulated environment, or other activities such as age-appropriate graphical puzzles to be solved.

The input detection subsystem 354 is responsible for detecting the patient's input, either by wand, mouse, keyboard, voice recognition or other input selection device, and applying the results of the patient's selection. For example, where the patient is tasked with identifying a distant object, the patient may have a row of icons on the bottom of the patient's view representing the entire set of objects available to be displayed. When the patient can identify the displayed object, the patient will select the icon representing the object from the row of icons by pointing to the icon with the pointing device and selecting the icon, by pressing the correct key on the keyboard representing the icon, or by voice recognition or other selection mechanisms. Such additional selection mechanisms also enable the present invention to be used with younger children and the disabled. If the patient is using a selection device such as a wand or mouse to select the icons, the input detection subsystem 354 recognizes the coordinates in the simulated environment that the patient has selected, determines which icon is at the selected coordinates, and passes which icon was selected to the score manager subsystem 360.

The score manager subsystem 360 is responsible for determining whether the patient correctly identified the object. The score manager subsystem records whether the identification was successful or unsuccessful, and the visual acuity level of the object when the patient attempted to identify the object. The patient's results are recorded in the treatment output log 370.

At the end of the treatment session, the patient's treatment output log 370 is transferred back to the prescription utility program 310 and stored with the patient's information. The treatment output log 370 contains the information regarding the patient's session, including the length of time the patient used the system, the length of time the session was operated in occlusive mode for each eye, the length of time the system was operated in non-occlusive mode during the session, the number of correct and incorrect shape identifications, and the visual acuity level of each identification attempt. Once again, if the treatment program 330 and prescription utility program 310 are not located on the same computer system, the treatment output log 370 can either be transferred over a network or e-mail, or the treatment program can save the treatment output log 370 to a portable storage medium such as a floppy disk, compact disc, or flash memory stick that the patient can return to the clinician, or the treatment output log 370 could be communicated verbally or in writing to the clinician for the clinician to enter manually into the prescription utility program 310.

When the treatment session is over and the prescription utility program 310 has received the treatment output log 370, the treatment results are recorded in the patient history database. The clinician can review the most recent treatment results using the patient history subsystem 313, as well as reviewing the results of all treatment sessions. Additionally, the clinician can view a summary of the patient's treatment sessions using the patient progress tool 314.

Based on the results of the patient's treatment session, and the patient's overall progress, the clinician can either maintain the current prescription, or use the prescription creation and editing tool 312 to modify the patient's existing prescription. For example, if the patient has progressed faster or slower than the clinician projected, the clinician can reduce or increase the length of the treatment session or the amount of time each eye is occluded. When the patient starts the process again for the next treatment system, the new prescription 320 will be given to the treatment program 330 to control the patient's treatment session. The prescription utility program 310 can also be programmed by the clinician to automatically adjust the patient's prescription 320 for the next treatment session, or only adjust the treatment minutes after the clinician reviews the results. For example, if the patient quit the treatment program 330 before the required number of minutes of occlusion for the session, the prescription utility program 310 can read the treatment log, recognize the minutes deficiency, and because treatment times are additive, adjust the patient's prescription for the next treatment session to require the missed minutes per the clinician's programmed instructions. Also, other rules for setting the patient's prescription can be programmed into the prescription utility program 310 by the clinician. If the patient has correctly identified a certain number of objects at the prescribed visual acuity level, and per the clinician's specified instructions, the prescription utility program 310 can adjust the prescription to a more difficult visual acuity level during the next session. Additionally, the clinician can program the treatment system 330 to automatically adjust the visual acuity level of objects during a treatment session based on the object identification success rate during the session.

The clinician can also adjust the prescription based on the clinician's review of the patient's progress using standard office measurements. For example, the clinician can verify the treatment results using a standard office eye chart to judge the patient's visual acuity level in the amblyopic eye. If the patient has suffered a relapse in visual acuity level, the clinician can use the prescription creation and maintenance tool 312 to adjust the patient's prescription for the subsequent treatment sessions, including requiring longer and more frequent sessions. Additionally, the clinician can program the treatment system 330 to automatically adjust the prescription parameters during the treatment session.

In order to accurately measure occlusion time for each eye, the system can contain features designed to detect whether the patient is actually using the system. For example, if the patient needs to quit the treatment system 330 during a treatment session, the patient can indicate using the wand or other selection device, and the system will stop the treatment program and record the actual compliance time. The system can also contain a pause function to allow the patient to take a short break from the application, and resume the application once the patient returns. During such a break, the system would not record any occlusion time. The treatment program can also determine whether or not the patient is actively using the system. For example, if the patient has not moved in the simulated environment, used the pointing device to select an object or the system has not detected movement of the magnetic position sensor FIG. 1, 51 for a specified amount of time, the treatment program can assume that the patient is no longer actively using the system. In such cases, the treatment system can stop recording any occlusion time until the patient performs some sort of activity in the application, and reduce the measured occlusion time to the last known activity performed by the patient to ensure an accurate measurement of occlusion time.

Figure 5:
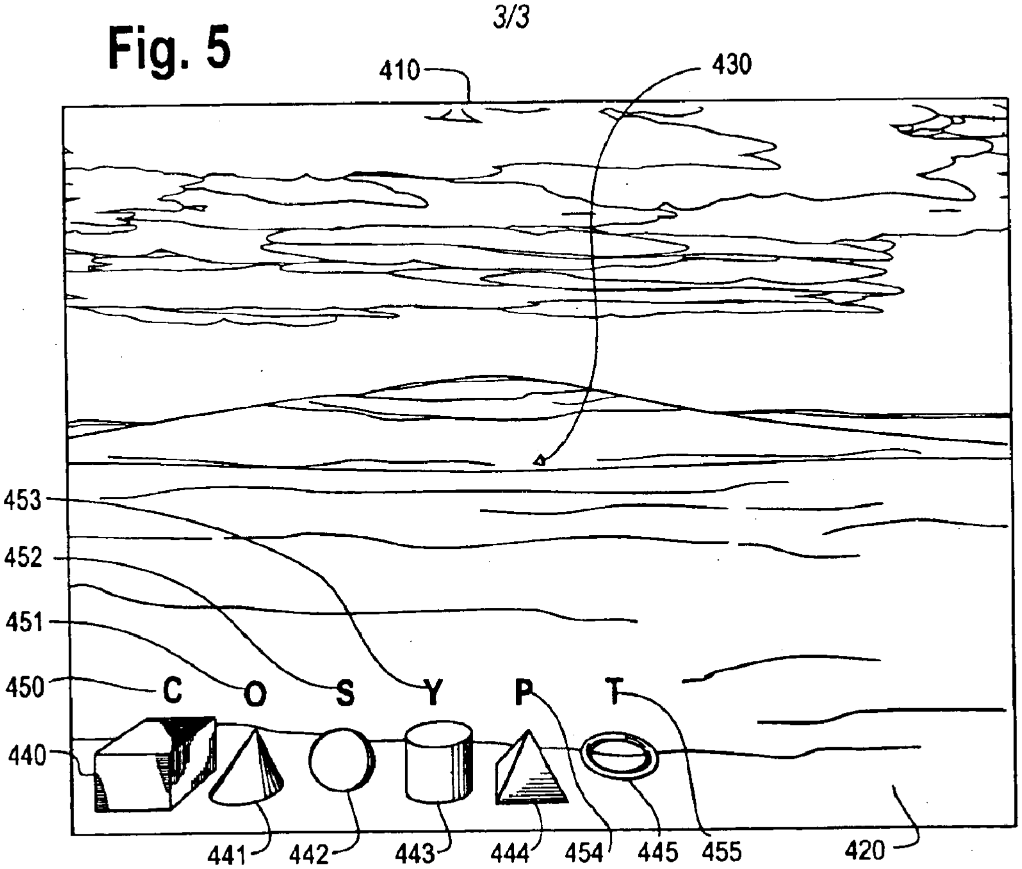
FIG. 5 is a screen capture of treatment system application showing distant object.

FIG. 5 shows a sample screen shot from one treatment application. The treatment application is preferably run in an immersive virtual reality system such as the CAVE of FIG. 1, but could also be run in a less immersive setting such as the monitor of FIG. 3. Referring to FIG. 1, in the CAVE, the treatment program of FIG. 4, 330 would be running on the central computer system 10, and the image displayed in FIG. 5 would be displayed by the image viewer of FIG. 4, 351 and projected on the walls 5, 6, 7 and floor 8 of the CAVE. The patient viewing the display would perceive himself or herself as standing on the ground of FIG. 5, 420 that would be projected on the walls and floor 5, 6, 7, 8, and the sky would be projected on the top of the walls 5, 6, 7. The central computer system 10 would use its CAVElib software to determine how the image should be split across the different projectors 30, 31, 32 to achieve the immersive effect. Referring again to FIG. 5, the patient appears to be standing on the virtual ground 420 and looking at a virtual world. During the treatment session, the treatment program running on the central computer system determines when each eye should be occluded, and for how long, and sends the appropriate control signals to perform the occlusion.

The tasks performed in this embodiment of the invention include identifying an object at a programmable distance. The object shown in FIG. 5 is selected randomly from a set of available polyhedrons, although the set of objects could be any shapes recognizable to the patient, and the system may contain multiple sets of objects to display based on the age of the patient and the patient's preferences. The selected object is displayed to the user at a distance and size suitable to the patient's visual acuity level, as specified in the patient's prescription, FIG. 4, 320. Initially, the object FIG. 5, 430 should be displayed at a size and distance just outside the patient's visual acuity level, and gradually move closer to the patient until the patient can identify the object. Because the object is being displayed in virtual reality, the image is actually projected on the wall a certain fixed distance from the patient, but the object is scaled so that it will appear to the user as if the object were a certain size and a certain distance from the patient in the virtual world.

The CAVE system also eliminates the problem of angular magnification. In order to present an object sized at a certain visual acuity level at a certain distance, as discussed above the visual angle subtended by the object at the patient's eye must be equivalent to the visual angle for the appropriate visual acuity level. For example, if an object is sized at a 20/20 visual acuity level and the object is displayed to appear at 20 feet from the patient, the object must subtend a visual angle of five minutes of arc at the patient's eye. If the patient moves closer to the object in the virtual world and the object's size is not changed, the object will subtend a larger angle at the patient's eye, and the visual acuity level that the object represents will increase. This can also occur by the patient changing actual position in the CAVE by physically walking forward towards the walls. Because the shutter glasses FIG. 1, 50 contain a magnetic position sensor 51, the position tracking device 60 can determine the exact physical distance the patient is from the projected display, the image viewer subsystem FIG. 4, 351 of the treatment program FIG. 4, 330 can adjust the size and distance of the displayed object to maintain the proper visual acuity size and distance. In the case of the computer monitor-driven system of FIG. 3, the patient could be fixed at a certain distance from the monitor using a headrest device, or a magnetic position sensor and position tracking device similar to FIG. 1, 51 and 60 could be incorporated into the system.

Figure 6:
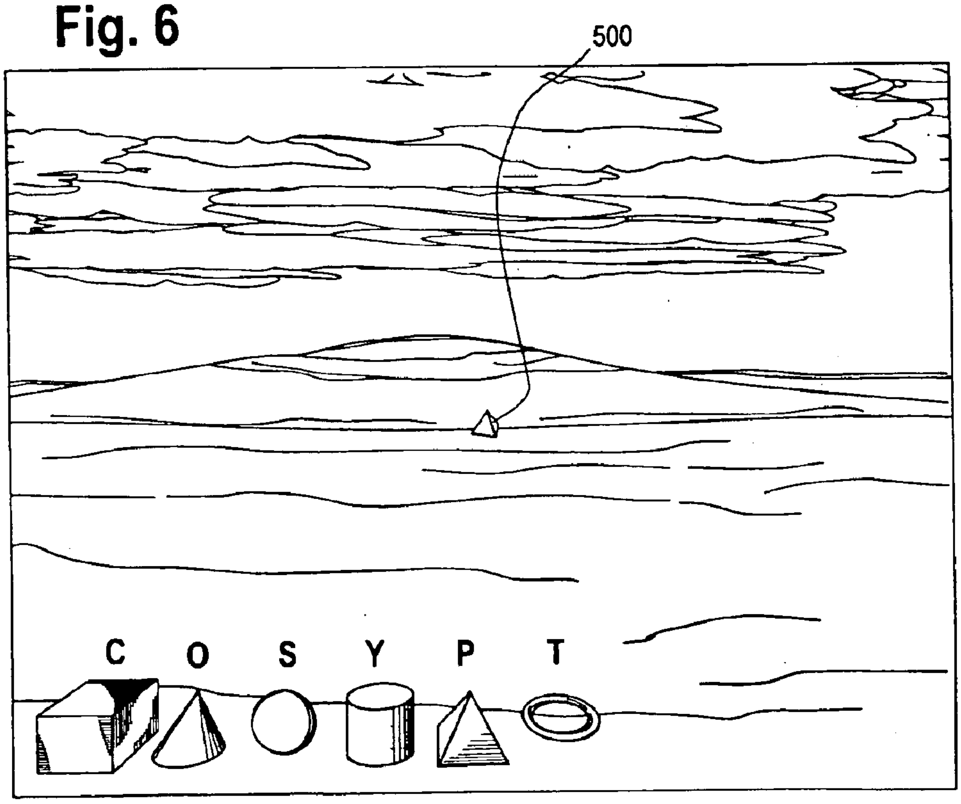
FIG. 6 is a screen capture of treatment system application showing medium-distance object.

Referring again to FIG. 5, the patient's view also contains a row of icons 440–445 indicating the entire set of polyhedrons available to be displayed to the patient. When the patient recognizes the displayed object 430, the patient uses the selection device such as the wand FIG. 1, 70, mouse or keyboard, to select the appropriate icon from the row of icons. The icon selection keys of FIG. 5, 450–455 show one possible selection mechanism by showing a letter indicating the key on the keyboard that a patient should press to identify the icon below the letter. The treatment program records the distance, visual acuity level of the object at the time of the identification attempt, and whether or not the attempt was successful. The treatment program can also provide a visual or audio signal to the patient to tell the patient whether the attempt was successful. The clinician can specify this preference in the prescription file FIG. 4,320 to account for the patient's abilities or disabilities. If the patient did not correctly identify the object, the system will allow the object to move closer to the user, increasing its visual acuity level. The represented size of the object remains constant as the object moves closer, but as the object becomes closer, angular magnification makes the image of the object appear larger to the patient. Therefore, the recorded visual acuity level will be correspondingly larger. FIG. 6 shows the object 500 of FIG. 5 appearing at a closer distance to the patient in the virtual world. If the patient has correctly identified the object 500 or the patient has not identified the object 500 after a specified amount of time, the treatment program FIG. 4, 330 will record the results and will use the image generator tool 353 to select the next object to display to the patient.

In order to prevent the patient from memorizing which objects will be presented in what order, the image generator tool should select the next object randomly from the set of available objects. The treatment program 330 also determines the size of the object to be displayed. Over the course of multiple treatment sessions, the goal of the treatment system is to present the patient with progressively smaller images in order to gradually improve the visual acuity level of the amblyopic eye. Based on the prescription 320, the treatment program determines at what visual acuity level objects should be sized for the initial images. During a treatment session, however, the treatment program 330 determines how the identification objects should be sized based on the patient's results during that session. The treatment program may be programmed such that, if the patient has correctly identified a certain number of objects at the specified visual acuity level, the system will reduce the visual acuity size of the objects to the next smallest visual acuity level to further work the amblyopic eye.

Additionally, the treatment program may also increase the size of the displayed objects for a certain amount of time in order to provide the amblyopic eye with rest, but also to ensure that the patient has actually reached the indicated visual acuity level on a sustained basis. If the patient is unable to identify objects at a larger visual acuity size then the patient's indicated progress, then the patient may have regressed. If treatment has not been regularly followed, such regression may occur and the patient's prescription should be adjusted to indicate the need for higher visual acuity level. The clinician may also indicate that more frequent or longer sessions are required.

In order to make the identification process more difficult, the image viewer FIG. 4, 351 can present the object as rotating and moving in space, either toward or away from the user. This makes the amblyopic eye work harder, making the system more interactive, physically fun and more effective as a treatment. If the patient is able to identify a rotating object, it is also more probable that the patient is improving toward a visual acuity level usable in real world situations, rather than the isolated conditions of a treatment system.

The treatment program can also increase the difficulty level to match real-world conditions in other ways. For example, in order to address concerns about crowding, the object to be identified could be placed in a virtual world with other objects. In the crowding phenomenon, patients are able to recognize spatial patterns at a smaller level of visual acuity when the object is isolated from other objects. When the spatial pattern is placed with other patterns, the patient has difficulty resolving the contours of the patterns with the amblyopic eye. In the real world, however, objects are not isolated, and the visual acuity level indicated by the identification of isolated objects is not the most reliable indication of the actual visual acuity level of the patient's amblyopic eye. In order to test crowding, the patient could be standing in a virtual forest, and the object could move between the trees. If the patient is unable to identify an object at a given visual acuity level, the image viewer subsystem could reduce the number of trees displayed, or even revert to an isolated object without trees to allow the patient to identify the object. The treatment program could even be programmed by the clinician to periodically test crowding, or periodically turn off crowding and use only isolated images to provide relief to the patient. The amount of objects used to test crowding and the frequency of crowding testing can also be recorded in the patient's treatment results and adjusted in the patient's prescription for the next treatment session.

The system can similarly test the patient's contrast sensitivity by increasing or decreasing the level of contrast in the displayed images. Color in computer graphics is usually represented by a triad of values, one for red, one for green and one for blue. This grouping is usually referred to as the RGB value of an object. Each component of the RGB value is in the range of 0 to 255, where 256 is the number of values available in 1 BYTE of data. To illustrate, an RGB value of 0, 0, 0 would be black, a value of 255, 0, 0 would be red, a value of 0, 255, 0 would be green, and a value of 0, 255, 255 would be cyan. Contrast is best expressed though in levels of gray, where gray is the range of colors from black (0, 0, 0) to white (255, 255, 255), and each member of the triad has the same value. There are essentially 256 levels of gray that are possible in computer graphics. Color contrast testing could be done by varying the gray level of an object with respect to another gray object or a gray background within $1/256^{th}$ of the contrast difference between black and white.

When treatment starts, the level of contrast can be set very high. Because the treatment application is using a virtual world, the contrast can be set higher than the real world. As the patient's treatment progresses and the patient's visual acuity level in the amblyopic eye improves, the contrast can be gradually reduced. The patient's contrast sensitivity level can be recorded in the treatment output log of FIG. 4, 370 and prescription file 320. The clinician can also adjust the contrast sensitivity in the patient's prescription file 320 based on standard contrast sensitivity tests in the clinician's office.

The ability to interact with the simulated environment, both by being able to move around the world as if in three-dimensional or two-dimensional space, as well as the ability to interact with objects in the simulated environment using the wand of FIG. 1, 70 or other pointing device allows the treatment to attain a level of physicality and present task-intensive activities for the patient to complete that will more effectively interest the patient and exercise the amblyopic eye. The use of the graphical treatment system can also allow the level of interactivity, and the setting of the treatment application, to be adjusted for the patient's age and interests in order to ensure that the patient is motivated to continue treatment. For example, younger patients can be shown simulated environments that contain bright colors and landscapes that look as if they were sketched using crayons or finger-painting. The patient could move around the simulated environment in a child's lawn traveler, and the patient could be required to identify child-recognizable animals such as birds, fish, or colorful insects. In one example, the patient could be carrying a virtual insect net, and when the patient can identify a specific insect, the patient can snag the appropriate insect icon with the insect net. Of course, during the application, the central computer system is still measuring the occlusive and non-occlusive time periods, as well as the number of identification attempts, the visual acuity size level of each insect when the patient makes an attempt, and the accuracy of such attempts. Based on the patient's success, the treatment program can increase or decrease the size or distance of the insects for the appropriate treatment programming. Other appropriate treatment applications would be known to those skilled in the art. For example, medium-age patients could run a treatment application where the patient is required to interact with animals, such as rabbits that pop in and out of the visual scenario in order to keep the patient's interest. There can be visual acuity incentives or penalization for identifying or not identifying the pop-up objects in a specified amount of time. To address crowding, objects similar to the desired target object could be popping up to create confusion or decision making in choosing a target. While the confusing targets are present, there would be lateral rather than anterior-posterior movement until the time limit expires. Additionally, the rabbits could be chased by other animals such as foxes, and the rabbits can hold different objects such as carrots. This allows the application to present the patient with variously-sized objects, differing colors and differing goals. Any of the above objects size, of course, could be changed based on the patient's responses. The application, of course, will be recording for each activity, which eye is being occluded, the visual acuity level of the patient's target(s), and the success or failure of the patient's activities. Similarly, older patients may be presented with more sophisticated activities, such as fast-paced video games. For example, the patient could be required to attempt to shoot appropriately-sized incoming objects with a virtual laser beam by pointing the wand or other selection device at the object, and the treatment system would record the visual acuity level of the object when the patient attempted to shoot the object and whether the attempt was successful.

Ideally, the patient should not know which eye is occluded at any given time, and the system may even be able to operate without occlusion, such that if the patient is interested in the treatment application, the patient can continue playing after the treatment session time has ended. Once the patient has exceeded the prescribed occlusion time, however, the treatment program will operate the glasses and display such that neither eye is occluded to prevent increasing the risk of creating amblyopia in the sound eye. In order to measure such interactivity, the system can record in the patient's treatment log, and ultimately patient history file, the amount of not only occlusive time, but also non-occlusive time to allow the clinician to better judge the effectiveness and popularity of the treatment settings. More importantly, by reviewing the progress of multiple patients across multiple treatment sessions, and comparing the progress to the actual occlusion times recorded in the patient histories and summaries, the clinician can more accurately determine the required frequency and duration of treatment sessions, as well as the amount of occlusive and non-occlusive time necessary during such treatment sessions and create new prescriptions accordingly.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosures. The scope of the invention is to be defined only by the claims appended hereto, and by their equivalents.

What is claimed is:

1. An interactive occlusion system for treating amblyopia in a patient, comprising:

a display medium;

an occlusion device adapted to selectively occlude at least one of the patient's eyes; and a computer system coupled to said occlusion device and said display medium, where said computer system is adapted to:

operate a treatment application displayed on the display medium;

control said occlusion device to selectively occlude at least one of the patient's eyes;

sense the patient's active use of the interactive occlusion system;

record an amount of time the occlusion device is controlled to selectively occlude at least one of the patient's eyes during the period of recognition that the patient is actively using the interactive occlusion system; and record a visual acuity level of the patient.

2. The interactive occlusion system as claimed in claim 1, where the computer system further comprises a plurality of computers, the computer system is further adapted to transfer the recorded visual acuity level and the recorded amount of time the occlusion device is controlled to occlude at least one of the patient's eyes to a remote computer.

3. An interactive occlusion system for treating amblyopia in a patient, comprising:

a display medium;

an occlusion device adapted to selectively occlude at least one of the patient's eyes; and a computer system coupled to said occlusion device and said display medium, where said computer system is adapted to:

operate a treatment application displayed on the display medium;

control said occlusion device to selectively occlude at least one of the patient's eyes;

sense the patient's active use of the interactive occlusion system;

record an amount of time the occlusion device is controlled to selectively occlude at least one of the patient's eyes during the period of recognition that the patient is actively using the interactive occlusion system;

retrieve a stored prescription for the patient, where said prescription comprises a desired amount of time that at least one of the patient's eyes should be occluded, and operate the treatment application and control the occlusion device based on said prescription.

4. The interactive occlusion system as claimed in claim 3, where said computer system is further adapted to:

compare the recorded amount of time the occlusion device was controlled to occlude at least one of the patient's eyes with the desired amount of time at least one of the patient's eyes should be occluded; and control the occlusion device to not occlude either of the patient's eyes when said recorded amount of time the occlusion device was controlled to occlude at least one of the patient's eyes is greater than said desired amount of time at least one of the patient's eyes should be occluded.

5. The interactive occlusion system as claimed in claim 4, where said computer system is further adapted to record an amount of time the occlusion device is controlled to not occlude either of the patient's eyes.

6. The interactive occlusion system as claimed in claim 3, where said prescription further comprises a visual acuity level.

7. The interactive occlusion system as claimed in claim 3, where said computer system is further adapted to operate a prescription utility application, wherein said prescription utility application is adapted to retrieve and modify said stored prescription.

8. The interactive occlusion system as claimed in claim 7, where said prescription utility application is further adapted to:

retrieve the recorded amount of time the occlusion device was controlled to selectively occlude at least one of the patient's eyes; and modify said stored prescription based on the recorded amount of time the occlusion device was controlled to selectively occlude at least one of the patient's eyes.

9. The interactive occlusion system as claimed in claim 8, where the computer system further comprises a plurality of computers, the prescription utility application and treatment application are operated on separate computers.

10. The interactive occlusion system as claimed in claim 3 where the prescription further comprises the desired amount of time at least one of the patient's eyes should be occluded across a plurality of treatment sessions, and the computer system is further adapted to:

record an amount of time the occlusion device is controlled to selectively occlude at least one of the patient's eyes across a plurality of treatment sessions;

compare the amount of time the occlusion device was controlled to selectively occlude at least one of the patient's eyes across the plurality of treatment sessions with the desired amount of time at least one of the patient's eyes should be occluded across the plurality of treatment sessions; and operate the treatment application and control the occlusion device based on said comparison.

11. The interactive occlusion system as claimed in claim 10, where the computer system is further adapted to control the occlusion device to not occlude either of the patient's eyes when the recorded amount of time the occlusion device was controlled to selectively occlude at least one of the patient's eyes across the plurality of treatment sessions is greater than the desired amount of time at least one of the patient's eyes should be occluded across the plurality of treatment sessions.

12. An interactive occlusion system for treating amblyopia in a patient, comprising:

a display medium;

an occlusion device adapted to selectively occlude at least one of the patient's eyes; and a computer system coupled to said occlusion device and said display medium, where said computer system is adapted to:

operate a treatment application displayed on the display medium;

control said occlusion device to selectively occlude at least one of the patient's eyes;

sense the patient's active use of the interactive occlusion system;

record an amount of time the occlusion device is controlled to selectively occlude at least one of the patient's eyes during the period of recognition that the patient is actively using the interactive occlusion system; and authenticate the patient's identity, and control the occlusion device to operate without occluding either of the patient's eyes if the computer system is unable to authenticate the patient's identity.

13. An interactive occlusion system for treating amblyopia in a patient, comprising:

a display medium;

an occlusion device adapted to selectively occlude at least one of the patient's eyes; and a computer system coupled to said occlusion device and said display medium, where said computer system is adapted to:

operate a treatment application displayed on the display medium, where the computer system is further adapted to select the treatment application from a plurality of available treatment applications based on the patient's age;

control said occlusion device to selectively occlude at least one of the patient's eyes;

sense the patient's interaction with the treatment application; and record an amount of treatment time the occlusion device is controlled to selectively occlude at least one of the patient's eyes during the period of recognition that the patient is interacting with the treatment application.

14. An interactive occlusion system for treating amblyopia in a patient, comprising:

a display medium;

an occlusion device adapted to selectively occlude at least one of the patient's eyes;

a computer system coupled to said occlusion device and said display medium, where said computer system is adapted to:

operate a treatment application displayed on the display medium;

control said occlusion device to selectively occlude at least one of the patient's eyes;

sense the patient's active use of the interactive occlusion system; and record an amount of time the occlusion device is controlled to selectively occlude at least one of the patient's eyes during the period of recognition that the patient is actively using the interactive occlusion system; and a position tracking device coupled to the computer system adapted to track the position of the patient's eyes, where the computer system is further adapted to receive the position of the patient's eyes from the position tracking device and operate the treatment application based on the position of the patient's eyes.

15. A method for treating amblyopia in a patient, comprising the steps of:

providing a display medium;

providing an occlusion device adapted to selectively occlude at least one of the patient's eyes;

providing a computer system coupled to said display medium and occlusion device;

providing a treatment application;

operating the treatment application;

displaying output of said treatment application on said display medium;

controlling said occlusion device to selectively occlude at least one of the patient's eyes;

sensing the patient's active use of the computer system, display medium and occlusion device;

recording an amount of time at least one of the patient's eyes was occluded during the period of recognition that the patient is actively using the computer system, display medium and occlusion device; and recording a visual acuity level of the patient.

16. The method as claimed in claim 15, where the computer system is a plurality of computers, further comprising the step of transferring the recorded visual acuity level and the recorded amount of time the occlusion device was controlled to occlude at least one of the patient's eyes to a remote computer.

17. A method for treating amblyopia in a patient, comprising the steps of:

providing a display medium;

providing an occlusion device adapted to selectively occlude at least one of the patient's eyes;

providing a computer system coupled to said display medium and occlusion device;

providing a treatment application;

operating the treatment application;

displaying output of said treatment application on said display medium;

controlling said occlusion device to selectively occlude at least one of the patient's eyes;

sensing the patient's active use of the computer system, display medium and occlusion device;

recording an amount of time at least one of the patient's eyes was occluded during the period of recognition that the patient is actively using the computer system, display medium and occlusion device;

retrieving a stored prescription for the patient, where said prescription comprises a desired amount of time that at least one of the patient's eyes should be occluded; and wherein said steps of operating the treatment application and controlling the occlusion device are based on said prescription.

18. The method as claimed in claim 17, further comprising the steps of:

comparing the recorded amount of time the occlusion device was controlled to occlude at least one of the patient's eyes with the desired amount of time at least one of the patient's eyes should be occluded; and controlling the occlusion device to not occlude either of the patient's eyes when said recorded amount of time the occlusion device was controlled to occlude at least one of the patient's eyes is greater than said desired amount of time at least one of the patient's eyes should be occluded.

19. The method as claimed in claim 17, where the prescription further comprises a visual acuity level.

20. The method as claimed in claim 17, further comprising the steps of:

providing a prescription utility application, and operating the prescription utility application to retrieve and modify said stored prescription.

21. The method as claimed in claim 20, further comprising the step of receiving the recorded amount of time the occlusion device was controlled to selectively occlude at least one of the patient's eyes, wherein the step of operating the prescription utility application is based on the recorded amount of time the occlusion device was controlled to selectively occlude at least one of the patient's eyes.

22. The method as claimed in claim 21, wherein the steps of operating the treatment application and prescription utility application are performed on separate computers.

23. The method as claimed in claim 17 wherein the prescription further comprises the desired amount of time at least one of the patient's eyes should be occluded across a plurality of treatment sessions, further comprising the steps of:

recording an amount of time the occlusion device was controlled to selectively occlude at least one of the patient's eyes across the plurality of treatment sessions;

comparing the amount of time the occlusion device was controlled to selectively occlude at least one of the patient's eyes across the plurality of treatment sessions with the desired amount of time at least one of the patient's eyes should be occluded across the plurality of treatment sessions; and wherein the steps of operating the treatment application and controlling the occlusion device are based on said comparison.

24. The method as claimed in claim 23 wherein the step of controlling the occlusion device further comprises controlling the occlusion device to not occlude either of the patient's eyes when the recorded amount of time the occlusion device was controlled to selectively occlude at least one of the patient's eyes across the plurality of treatment sessions is greater than the desired amount of time at least one of the patient's eyes should be occluded across the plurality of treatment sessions.

25. The method as claimed in claim 24, further comprising the step of recording an amount of time the patient's eyes were not occluded.

26. The method as claimed in claim 17, further comprising the steps of:

providing a plurality of available treatment applications; and wherein the step of providing a treatment application further comprises selecting the treatment application from the plurality of available treatment applications based on the patient's age.

27. A method for treating amblyopia in a patient, comprising the steps of:

providing a display medium;

providing an occlusion device adapted to selectively occlude at least one of the patient's eyes;

providing a computer system coupled to said display medium and occlusion device;

providing a treatment application;

operating the treatment application;

displaying output of said treatment application on said display medium;

controlling said occlusion device to selectively occlude at least one of the patient's eyes;

sensing the patient's active use of the computer system, display medium and occlusion device;

recording an amount of time at least one of the patient's eyes was occluded during the period of recognition that the patient is actively using the computer system, display medium and occlusion device; and authenticating the patient's identity and controlling the occlusion device to not occlude either of the patient's eyes if the computer system is unable to authenticate the patient's identity.

28. A method for treating amblyopia in a patient, comprising the steps of:

providing a display medium;

providing an occlusion device adapted to selectively occlude at least one of the patient's eyes;

providing a computer system coupled to said display medium and occlusion device;

providing a treatment application;

operating the treatment application;

displaying output of said treatment application on said display medium;

controlling said occlusion device to selectively occlude at least one of the patient's eyes;

sensing the patient's active use of the computer system, display medium and occlusion device;

recording an amount of time at least one of the patient's eyes was occluded during the period of recognition that the patient is actively using the computer system, display medium and occlusion device;

providing a position tracking device adapted to identify the position of the patient's eyes relative to the display medium; and receiving the position of the patient's eyes from the position tracking device, wherein the step of operating the treatment application is based on the position of the patient's eyes.

* * * * *

UNITED STATES PATENT AND TRADEMARK OFFICE
CERTIFICATE OF CORRECTION

PATENT NO. : 7,033,025 B2
APPLICATION NO. : 10/150310
DATED : April 25, 2006

INVENTOR(S) : Chloe Tyler Winterbotham

It is certified that error appears in the above-identified patent and that said Letters Patent is hereby corrected as shown below:

Column 12, line 25, delete " ' "

Column 26, line 22, after "eyes" insert -- relative to the display medium --

Column 28, line 54, delete "identify" and insert -- track --

Signed and Sealed this

Twelfth Day of September, 2006

JON W. DUDAS

*Director of the United States Patent and Trademark Office*